(12) United States Patent
Schlagheck et al.

(10) Patent No.: US 7,401,976 B1
(45) Date of Patent: Jul. 22, 2008

(54) DETECTION OF DEFECTS BY THERMOGRAPHIC ANALYSIS

(75) Inventors: Jerry Schlagheck, West Chester, OH (US); Marc Pastor, Saint-Hubert (CA)

(73) Assignee: ART Advanced Research Technologies Inc., Saint-Laurent, Quebec (CA)

( * ) Notice: Subject to any disclaimer, the term of this patent is extended or adjusted under 35 U.S.C. 154(b) by 379 days.

(21) Appl. No.: 09/648,140

(22) Filed: Aug. 25, 2000

(51) Int. Cl.
*G01N 25/72* (2006.01)
(52) U.S. Cl. ............................................. 374/5; 374/57
(58) Field of Classification Search ...................... 374/4, 374/5, 43, 57, 120–121, 124, 129, 137
See application file for complete search history.

(56) References Cited

U.S. PATENT DOCUMENTS

| | | | | |
|---|---|---|---|---|
| 5,032,727 | A * | 7/1991 | Cox et al. ................... | 250/330 |
| 5,208,528 | A | 5/1993 | Quintard | |
| 5,292,195 | A * | 3/1994 | Crisman, Jr. ................. | 250/330 |
| 5,358,333 | A * | 10/1994 | Schmidt et al. ................ | 374/5 |
| 5,440,566 | A * | 8/1995 | Spence et al. ................. | 374/41 |
| 5,649,766 | A * | 7/1997 | Blake ........................ | 374/137 |
| 5,657,075 | A * | 8/1997 | Roessner .................... | 348/126 |
| 5,775,806 | A | 7/1998 | Allred | |
| 5,834,661 | A * | 11/1998 | Nonaka et al. ................. | 374/5 |
| 5,984,522 | A * | 11/1999 | Koizumi ....................... | 374/5 |
| 6,000,844 | A * | 12/1999 | Cramer et al. .................. | 374/5 |
| 6,033,107 | A * | 3/2000 | Farina et al. ................... | 374/5 |
| 6,146,014 | A * | 11/2000 | Bruce et al. .................. | 374/120 |
| 6,271,520 | B1 * | 8/2001 | Tao et al. ..................... | 250/330 |
| 6,340,817 | B1 * | 1/2002 | Gelbart ....................... | 250/341.6 |
| 6,343,874 | B1 * | 2/2002 | Legrandjacques et al. ....... | 374/5 |
| 6,375,347 | B1 * | 4/2002 | Bruce et al. ..................... | 374/5 |
| 6,686,602 | B2 * | 2/2004 | Some ..................... | 250/559.45 |
| 6,798,505 | B2 * | 9/2004 | Karpol et al. ............. | 356/237.5 |
| 6,924,891 | B2 * | 8/2005 | Karpol et al. ............. | 356/237.5 |

* cited by examiner

*Primary Examiner*—Yaritza Guadalupe-McCall
(74) *Attorney, Agent, or Firm*—Fay Sharpe LLP

(57) ABSTRACT

A mechanism is provided for detecting a defect in a populated sample having a thickness dimension substantially smaller than the length and width dimensions thereof, the populated sample having a first side and an opposite second side, at least said first side of said populated sample having one or more Surface Mounted Components. The mechanism exploits a standard thermographic image which may be used in a detection method comprising
1) directing a thermal wave at said second side of said populated sample
2) recording a thermographic image of the first side of said populated sample once a surface thereof reaches a predetermined transit temperature or a predetermined transit time period has elapsed; and
3) analysing the obtained thermographic image by comparing the so obtained thermographic image with a standard thermographic image.

6 Claims, 4 Drawing Sheets

DETECTION OF DEFECTS BY THERMOGRAPHIC ANALYSIS

The present invention relates to the detection of defects in an object by means of thermal analysis.

Although the invention may be used for other types of (analogous) products the invention will be discussed herein in relation to printed circuit boards by way of example only, i.e. insulating base boards (e.g. epoxy resin boards) populated with electronic components such as resistor, transistors, integrated circuits, etc. . . . . These components are usually soldered to a base board; such solder joints are a source of defects, i.e. defects due to absence or poor quality of the solder joint.

It is known that an object such as a populated circuit board may be inspected for defects by a procedure wherein such a board is heated in order to obtain a thermographic image. The obtained image is then analysed by being compared to a standard thermo graphic image of a defect free populated circuit board; i.e. one image is differenced from the other. Please see for example U.S. Pat. Nos. 5,208,528 and 5,775,806, the entire contents of which are incorporated herein by reference.

It would be advantageous to have a method which facilitates the obtaining of images under conditions of high thermal contrast. It would in particular be advantageous to be able to tune out background thermal noise attributable to thermal characteristics of a base board itself.

It would be advantageous to be able to use or exploit an array of discrete heat sources during a thermal analysis; each individual heat source element may, for example, be an infrared light emitting diode. It would be advantageous to be able to use the array in the context of inspecting sample objects such as, for example, electronic circuit boards.

It would in particular be advantageous with respect to circuit boards to have an inspection technology based on an apparatus which is relatively easy to make and use and which relatively more reliable. It would more particularly be advantageous for example to have a method system apparatus etc. which may be exploited to inspect a circuit card without the use of an isothermal housing.

STATEMENT OF INVENTION

The present invention in accordance with one aspect relates to an (infrared) inspection system for the detection of an anomaly (defects) in a sample comprising
- a thermal heater array comprising a plurality (e.g. of rows and columns of) discrete individually controllable heat source elements capable of imparting heat (i.e. thermal radiation) to a sample (an examination object)
- a heat diffuser component
- an infrared camera component for monitoring infrared emissions from a side of the sample and deriving a signal indicative of the temperature (profile) of this side of the sample.
- a sample support component for supporting a sample for inspection said sample support component, said heat diffuser component and said thermal heater array being configured and disposed such that, when said support component supports a sample for inspection, the sample has an observation side and an opposite heat exposure side, the infrared camera is disposed on the observation side for monitoring the observation side and the diffuser component and the thermal heater array are disposed on the heat exposure side for exposing the heat exposure side to thermal radiation, the heat diffuser component being disposed between the sample and the thermal heater array.

The present invention in accordance with a related aspect provides a method for obtaining a standard thermographic image (video, still, monitor, etc.) for use in detecting a defect in a populated sample having a thickness dimension substantially smaller than the length and width dimensions thereof, said sample having a first side and a second opposite side, at least said first side of said populated sample having one or more Surface Mounted Components, said method comprising a) monitoring the temperature of a surface of the first side of an predetermined unpopulated sample
b) subjecting the second side of the unpopulated sample to a thermal wave developed by a thermal heater array comprising a plurality of discrete individually controllable heat source elements, said elements each being initially set to deliver an individual energy intensity (i.e. deliver an energy load) such that the thermal array delivers a thermal wave of predetermined contour;
c) adjusting the individual energy intensity of each of said elements until the thermal array delivers a thermal wave such that the surface being monitored provides a recorded thermographic image thereof indicative of uniform temperature
d) storing (e.g. electronically-computer memory means) a first block of energy parameter information corresponding to the individual energy intensity (i.e. deliverable energy load) of each of said heat source elements found to provide the recorded thermographic image indicative of uniform temperature
e) monitoring the temperature of the first side of a predetermined populated sample
f) subjecting the second side of the predetermined populated sample to a thermal wave developed by a thermal heater array comprising a plurality of discrete individually controllable heat source elements, said elements each being set to deliver a respective individual energy intensity (i.e. deliver an thermal energy load) reflecting the energy parameter information of said first block of energy parameter information, said thermal wave being applied until a surface site reaches a predetermined transit temperature or a predetermined transit time period has elapsed and taking (i.e. recording or capturing) a second thermographic image (e.g. by infra red camera-video or still); and, if desired,
g) storing (e.g. electronically-computer memory means, etc. . . . ) a block of image information corresponding to the second thermographic image, said second thermographic image being said standard thermographic image. The (standard) thermographic image(s) may as desired be presented on a computer monitor or be reduced to a hard copy picture format using a suitable colour printer.

In accordance with a further aspect the present invention provides a method for detecting a defect in a populated sample having a thickness dimension substantially smaller than the length and width dimensions thereof, said sample having a first side and an opposite second side, at least said first side being populated with one or more Surface Mounted Components, said method comprising 1) directing a thermal wave (i.e. field or front) at said second side of said populated sample
2) recording a thermographic image of the first side of said populated sample once a surface thereof reaches a predetermined transit temperature or a predetermined transit time period has elapsed; and 3) analysing the obtained thermographic image by comparing the so obtained thermographic image with a standard thermographic image wherein
a) the thermal wave (i.e. field or front) is developed by a thermal heater array comprising a plurality of discrete individually controllable heat source elements, said elements each delivering a respective individual energy intensity (i.e. deliver an thermal energy load) reflecting the respective energy parameter information (e.g. intensity, duration, etc. . . . ) therefor comprised in a first block of energy parameter information (e.g. intensity, duration, etc. . . . );
b) said first block of energy parameter information comprising, for each of said heat source elements, individual energy parameter information whereby the thermal heater array may be induced (i.e. in response thereto) to provide a thermal wave giving rise to a thermographic image (i.e. as an image captured by an infra red camera-video or still) indicative of uniform temperature of the surface of the first side of a predetermined unpopulated sample (i.e. no Surface Mounted Components on either side thereof); and
c) said standard thermographic image having been obtained by i) subjecting the second side of a predetermined (e.g. defect free) populated sample to a thermal wave (i.e. field or front) developed by said thermal heater array, said thermal field being applied until a surface of the first side of the sample reaches said predetermined transit temperature, said elements of said thermal heater array each being set to deliver a respective individual energy intensity (i.e. deliver an energy load) reflecting the energy parameter information of said first block of energy parameter information, and
ii) taking (i.e. recording or capturing) said standard thermographic image (i.e. as an image captured by an infra red camera-video or still) from the first side of said predetermined populated sample once said predetermined temperature is reached or said predetermined transit time period has elapsed.

In accordance with an additional aspect the present invention provides a method for obtaining a standard thermographic image for use in detecting a defect in a populated circuit board, said populated circuit board having a first side and a second opposite side, at least said first side being populated with one or more Surface Mounted Components, said method comprising
a) monitoring the temperature of a surface of the first side of an predetermined unpopulated circuit board
b) subjecting the second side of the unpopulated circuit board to a thermal wave developed by a thermal heater array comprising a plurality of discrete individually controllable heat source elements, said elements each being initially set to deliver an individual energy intensity (i.e. deliver an energy load) such that the thermal array delivers a thermal wave of predetermined contour;
c) adjusting the individual energy intensity of each of said elements until the thermal array delivers a thermal wave such that the surface being monitored provides a thermographic image thereof indicative of uniform temperature
d) storing (e.g. electronically-computer memory means-video-hard copy picture) a first block of energy parameter information corresponding to the individual energy intensity (i.e. deliverable energy load) of each of said heat source elements found to provide the recorded thermographic image indicative of uniform temperature
e) monitoring the transit temperature of the first side of a predetermined populated circuit board
f) subjecting the second side of the predetermined populated circuit board to a thermal wave developed by a thermal heater array comprising a plurality of discrete individually controllable heat source elements, said elements each being set to deliver a respective individual energy intensity (i.e. deliver an energy load) reflecting the energy parameter information of said first block of energy parameter information, said thermal wave being applied until a surface site of the first side of the predetermined populated circuit board reaches said predetermined transit temperature or said predetermined transit time period has elapsed and taking (i.e. recording or capturing) a second thermographic image; and, if desired,
g) storing (e.g. electronically-computer memory means-video-hard copy picture, etc. . . . ) a block of image information corresponding to the second thermographic image, said second thermographic image being said standard thermographic image.

In accordance with the present invention there is also provided a method for detecting a defect in a populated sample having a thickness dimension substantially smaller than the length and width dimensions thereof, said populated sample having a first side and a second opposite side, at least said first side of said populated sample having one or more Surface Mounted Components, said method comprising
1) directing a thermal wave (i.e. field or front) at the second side of said populated sample
2) recording (e.g. electronically-computer memory means-video-hard copy picture, etc. . . . ) a thermographic image of the first side of said populated sample once a predetermined transit temperature is reached on this side of the populated sample or a predetermined transit time period has elapsed; and
3) analysing the obtained thermographic image by comparing (e.g. picture image by picture image, pixel by pixel, etc. . . . ) the so obtained thermographic image with a standard thermographic image (e.g. electronic image (monitor)-video image-hard copy picture) wherein the standard thermographic image has been obtained by
a) monitoring the temperature of a surface of the first side of an predetermined unpopulated sample
b) subjecting the second side of the predetermined unpopulated sample to a thermal wave developed by a thermal heater array comprising a plurality of discrete individually controllable heat source elements, said elements each being initially set to deliver an individual energy intensity such that the thermal array delivers a thermal wave of predetermined contour;
c) adjusting the individual energy intensity (i.e. deliverable energy load) of each of said elements until the thermal array delivers a thermal wave such that the surface being monitored provides a thermographic image thereof indicative of uniform temperature
d) storing (e.g. electronically-computer memory means-video-hard copy picture, etc. . . . ) a first block of energy parameter information corresponding to the individual energy intensity (i.e. derivable energy load) of each of said heat source elements found to provide the recorded thermographic image indicative of uniform temperature
e) monitoring the temperature of the first side of a predetermined (e.g. defect free) populated sample f) subjecting the second side of the predetermined (e.g. defect free) populated sample to a thermal wave developed by a thermal heater array comprising a plurality of discrete individually controllable heat source elements, said elements each being set to deliver a respective individual energy intensity (i.e. deliver an energy load) reflecting the energy parameter information of said first block of energy parameter information, said thermal wave being applied until a surface site reaches said predetermined transit temperature or said predetermined transit time period has elapsed and taking (i.e. recording or capturing) a second thermographic image; and, if desired g) storing (e.g. electronically-computer memory means-video-hard copy picture, etc. . . . ) a second block of image information corresponding to the second recorded thermographic image, said second recorded image being said standard thermographic image.

In accordance with a further aspect the present invention provides a method for detecting a defect in a populated circuit board, said populated circuit board having a first side and an opposite second side, at least said first side being populated with one or more Surface Mounted (e.g. soldered) Components, (i.e. said second side may be unpopulated or also populated with Surface Mounted (e.g. soldered) Components as desired or necessary), said method comprising 1) directing a thermal wave (i.e. field or front) at said second side of said populated circuit board
2) recording a thermographic image of the first side of said populated circuit board once a surface thereof reaches a predetermined transit temperature or a predetermined transit time period has elapsed; and
3) analysing the obtained thermographic image by comparing the so obtained thermographic image with a standard thermographic image wherein a) the thermal wave is developed by a thermal heater array comprising a plurality of discrete individually controllable heat source elements, said elements each delivering a respective individual energy intensity (i.e. deliverable energy load) reflecting the respective energy parameter information therefor comprised in a first block of energy parameter information;
b) said first block of energy parameter information comprising, for each of said heat source elements, individual energy parameter information whereby the thermal heater array may be induced (i.e. in response thereto) to provide a thermal wave (i.e. field) giving rise to a thermographic image (e.g. an image captured by an infra red camera-video/still, etc. . . . ) indicative of uniform temperature of the (a) surface of the first side of an predetermined unpopulated circuit board (i.e. a board with no Surface Mounted Components on either side); and
c) said standard thermographic image having been obtained by i) subjecting the second side of a predetermined (e.g. defect free) populated circuit board to a thermal wave (i.e. field) developed by said thermal heater array, said thermal wave being applied until a surface of the first side of the predetermined (e.g. defect free) populated circuit board reaches said predetermined temperature, said elements of said thermal heater array each being set to deliver a respective individual energy intensity (i.e. deliver an energy load) reflecting the intensity information of said first block of intensity information, and ii) taking (i.e. recording or capturing) said standard thermographic image (e.g. by an infra red camera video/still, etc. . . . ) from the populated side of the circuit board once said predetermined temperature is reached.

In accordance with another aspect the present invention provides a method for detecting a defect in a populated circuit board, said populated circuit board having a first side and a second opposite side, at least said first side being populated with one or more Surface Mounted (e.g. soldered) Components, said method comprising 1) directing a thermal wave (i.e. field or front) at the second side of said populated circuit board
2) recording a thermographic image of the first side of the board once a predetermined transit temperature is reached (observed at a predetermined surfaces site) on this side of the populated circuit board or a predetermined transit time period has elapsed; and
3) analysing the obtained thermographic image by comparing the so obtained thermographic image with a standard thermographic image wherein the standard thermographic image has been obtained by a) monitoring the temperature of a surface of the first side of an predetermined unpopulated circuit board
b) subjecting the second side of the predetermined unpopulated circuit board to a thermal wave (i.e. field) developed by a thermal heater array comprising a plurality of discrete individually controllable heat source elements, said elements each being initially set to deliver an individual energy intensity (i.e. deliver an energy load) such that the array delivers a thermal wave of predetermined contour;
c) adjusting the individual energy intensity (i.e. deliverable energy load) of each of said elements until the array delivers a thermal wave such that the surface being monitored provides a thermographic image thereof indicative of uniform temperature
d) storing (e.g. electronically-computer memory means-video-hard copy picture, etc. . . . ) a first block of energy parameter information corresponding to the individual energy intensity of each of said heat source elements found to provide the recorded thermographic image indicative of uniform temperature
e) monitoring the temperature of the first side of a predetermined (e.g. defect free) populated circuit board
f) subjecting the second side of the predetermined (e.g. defect free) populated circuit board to a thermal wave developed by a thermal heater array comprising a plurality of discrete individually controllable heat source elements, said elements each being set (i.e. controlled) to deliver a respective individual energy intensity (i.e. deliver an energy load) reflecting the energy parameter information of said first block of intensity information, said thermal field being applied until a surface (site) of the first side of the predetermined (e.g. defect free) circuit board reaches a predetermined temperature, for example 30° C., and taking (i.e. recording or capturing) a second thermographic image; and, if desired,
g) storing (e.g. electronically-computer memory means-video-hard copy picture, etc. . . . ) a block of image information corresponding to the second thermographic image, said second thermographic image being said standard thermographic image.

The methodology, apparatus, systems etc. of the present invention may for example be used with electronic circuit boards wherein electronic components are attached to an underlying base board; such base boards do not have a homogeneous heat transfer characteristic across their entire cross section from one end thereof to the other, i.e. heat will travel slower through some parts of the base board as compared to other parts of the same base board.

In accordance with the thermal analysis technology of the present invention each of the discreet heat sources are to be individually connected in suitable manner to an electrical control device which in turn is connected to a controlling computer system comprising means for storing blocks of information each block of information corresponding to a respective recorded thermal image. The controlling computer would also be connected to an infra-red camera. The sample to be tested would be disposed such that the infra-red camera is on one side of the sample whereas the array of individual discreet heat sources will be on the opposite side of the sample.

A system in accordance with the present invention may be calibrated in a two step process.

The first calibration step is carried out in order to obtain and store in computer memory the parameter settings (i.e. intensity, shape, duration, repetition rate, etc.) for each individual discrete heating unit or element which after a heating cycle provides the surface of a standard sample (i.e. the base board on both sides thereof is component free) facing the infra-red camera with an at least essentially uniform (i.e. reference) temperature (i.e. the surface facing the infra-red camera will provide a video image of essentially uniform colour indicative of a homogeneous temperature across the surface thereof).

For this calibration a preselected target area on the base board where the emissivity is very close to 1 (0.95 minimum) is used as a temperature reference to monitor the temperature (or Infra-red radiations) of the board during the pre-heat phase (Bare Board or Populated Board), i.e. the individual intensity levels are manipulated with a view to obtain a uniform thermal profile across the board which reflects the average temperature of the target area.

In other words, once the individual parameters (e.g. intensity levels, etc.) of each of the discrete heat sources has been found which will provide the surface of the sample (i.e. base board) facing the camera with a uniform temperature, these parameters (e.g. intensity levels, etc) are placed into computer memory and will herein be referred to as the "standard homogeneous base board parameters".

The second step in the calibration process is to take a thermal image of a predetermined (e.g. defect free) "electronic circuit card", comprising an above mentioned base board on which is included electronic components. The obtained thermal image may then be used as a standard against which other thermal images of other "electronic circuit card" of the same construction are to be compared as discussed below.

For the second calibration step a standard or predetermined (e.g. defect free) "electronic circuit board" is placed into the system and the intensity levels of each of the individual discreet heat (i.e. thermal energy) sources is set by the computer at the values initially determined for the "standard homogeneous base board parameters". The "electronic circuit board" is then heated for a pre-determined time period and/or until an area of the upperside of the "electronic circuit board" facing the camera registers a pre-determined temperature. At this point, the computer places into memory the thermal image of the side of the circuit board facing the infra-red camera. This thermal image is then to be used as the "standard thermal image" of a defect free "electronic circuit board" or to be used as a member of a set of images to build a model (statistical or otherwise). For instance, a statistical model will need around 30 images to give a good confidence interval.

Once the above "standard homogeneous base board parameters" and "standard thermal image" are obtained for a given circuit board construction testing of a production line "electronic circuit board" may proceed as follows:
  i) each individual circuit board to be tested is subjected to a heating cycle exploiting the above mentioned "standard homogeneous base board intensity levels" for a pre-determined time and/or until an area of the upperside of the "electronic circuit board" facing the infra-red camera registers a pre-determined temperature.
  ii) Once the pre-determined time has passed or the predetermined temperature (e.g. Infra red radiation level) is achieved, the thermal image of the inspected circuit board is captured and compared with the "standard thermal image", i.e. the thermal image of the tested sample is compared to that of the "standard thermal image" in order to determine whether or not there is a defect based on differences between the two thermal images.

In essence the first "standard homogeneous base board intensity levels" is used so as to be able to essentially render the base board thermally transparent during inspection of a sample "electronic circuit board".

In drawings which illustrate an example embodiment of the present invention:

Figure 1:
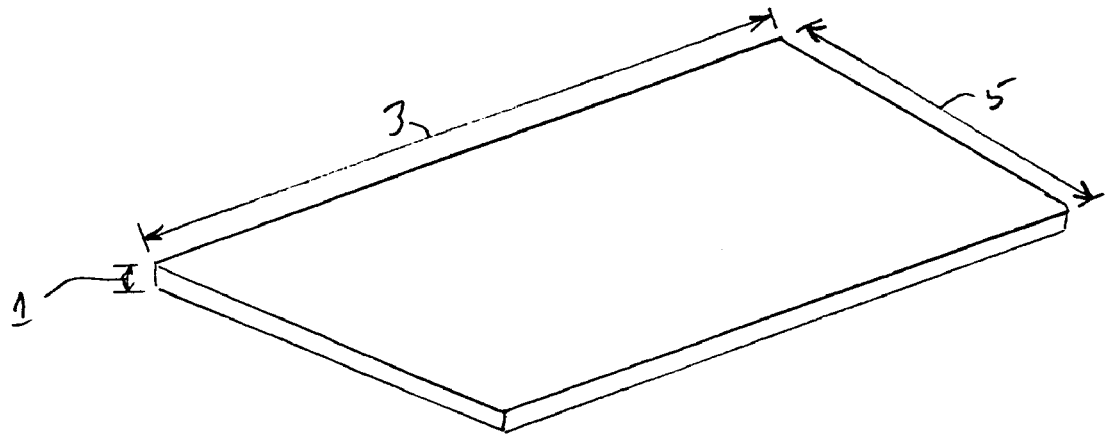
FIG. 1 is a schematic perspective side view of a base (i.e. unpopulated) circuit board (i.e. no Surface Mounted Components on either broad side thereof)
Figure 2:
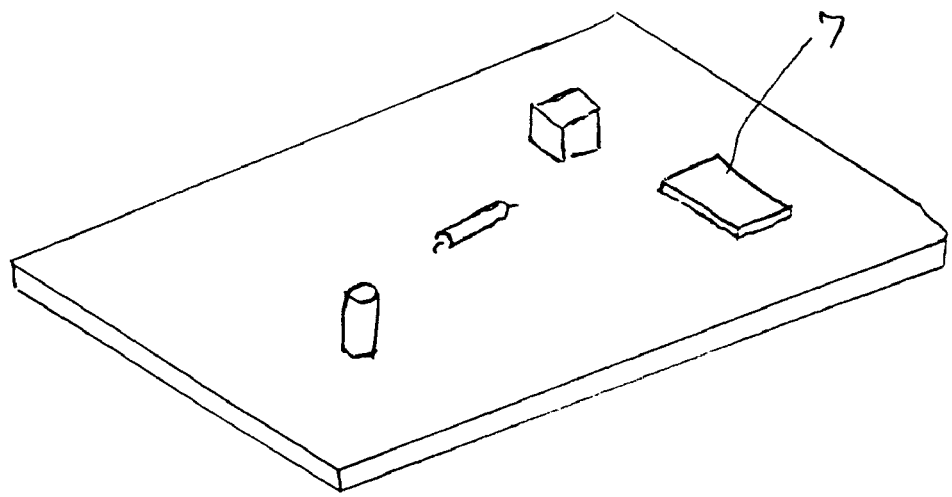
FIG. 2 is a schematic perspective side view of a populated circuit board (i.e. Surface Mounted Components on disposed on one board side thereof)

Referring to FIGS. 1 and 2 these figures respectively illustrate example samples, namely an unpopulated circuit board and a populated circuit board. The unpopulated sample and the populated sample each having a thickness dimension 1 substantially smaller than the length and width dimensions (3, 5) thereof. The samples each have a first (broad) side and an opposite second (broad) side. As may be seen from FIG. 2, the populated board is provided on one side thereof with a number of Surface Mounted Components, one of which is designated with the reference numeral 7. Both sides of the populated board may however be provided with such Surface Mounted Components. The components may for example be solder mounted.

Figure 3:
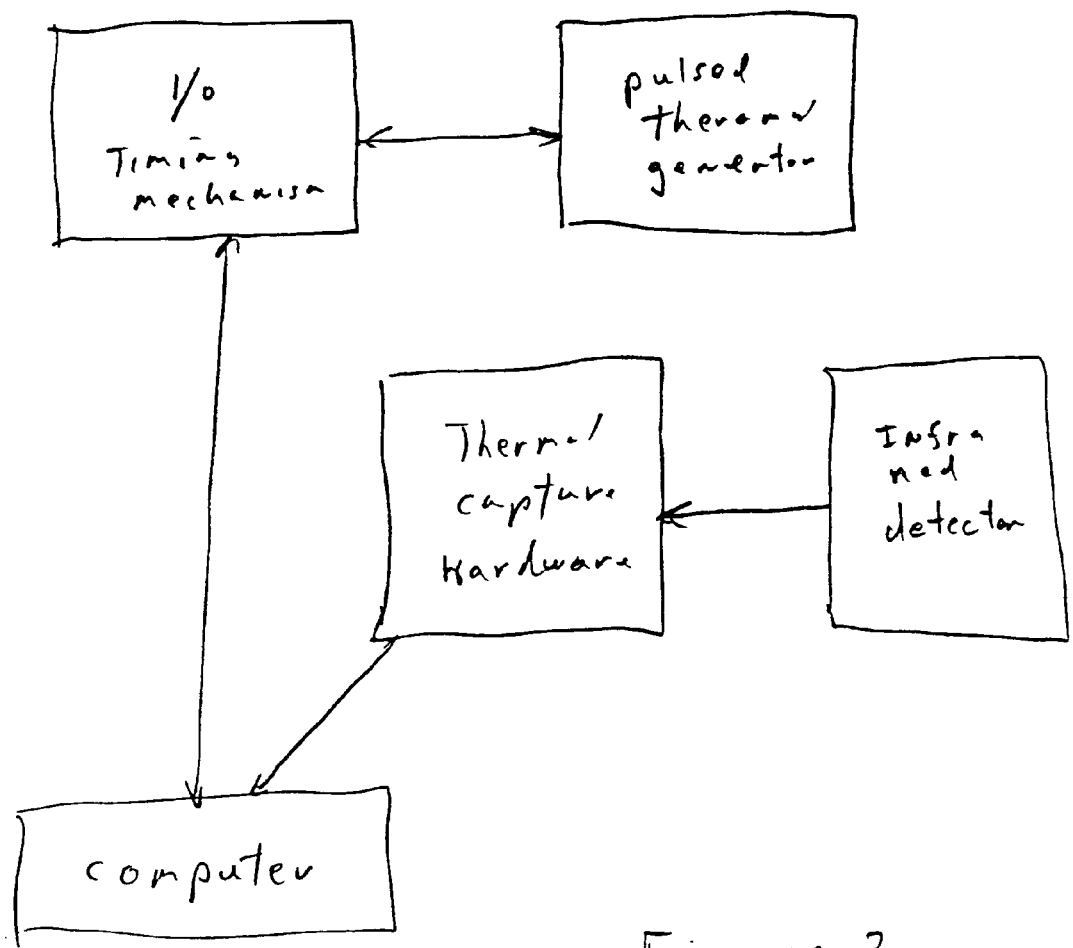
FIG. 3 is a block diagram of showing the operational components of an example system.

FIG. 3 shows a simplified block diagram of components of a thermal analysis system of the present invention. The system comprise a computer which is suitably connected to a an I/O timing mechanism as well as to thermal image capture hardware. The system includes a pulsed thermal generator as well as an infra red detector. The computer is configured (i.e. with any suitable software) so as to be able to induce the generation of a shaped digital pulse (via a digital to analog converter) which connected to the thermal heater array so as to produce a correspondingly shaped thermal field or wave.

The pulse generated by the computer may be a square wave, a saw tooth wave, a half sine wave or any other form that it is desired or necessary so as to be able to apply sufficient or desired thermal stimulation in a desired or predetermined time (e.g. shortest) duration to the unit under test. The computer will simultaneously initiate a timing circuit to acquire data, initiate the thermal heater array in a free running capture mode, monitor the temperature of the target array and acquire data when triggered by an event (temperature threshold and time-out).

The system is configured in any suitable (known) manner such that at specific (predetermined) time duration or temperature threshold the computer will acquire a thermal image via an infra red detector (e.g. camera) which transfers the acquired thermal image data (image) to the computer by a suitable digital interface. The computer then will process the image against a previously calculated thermal standard (CTS). The CTS has both an upper and lower control limits and any thermal data found to be outside these limits may be displayed on a computer monitor as for example red (exceeding limit) or blue (exceeding lower limit). The computer is of course configured in any suitable fashion so as to automatically build and define a model by allowing the user to acquire image s of acceptable units device etc. . . . . The software may of course be designed so as to automatically define the CTS for each pixel of the infra red detector array. The computer may be configured in any suitable fashion so as to archive all acquired data in a Data Base Management System. The system may be configured so as to allow a user to recalculate the CTS and add/remove thermal images from the CTS.

Figure 4:
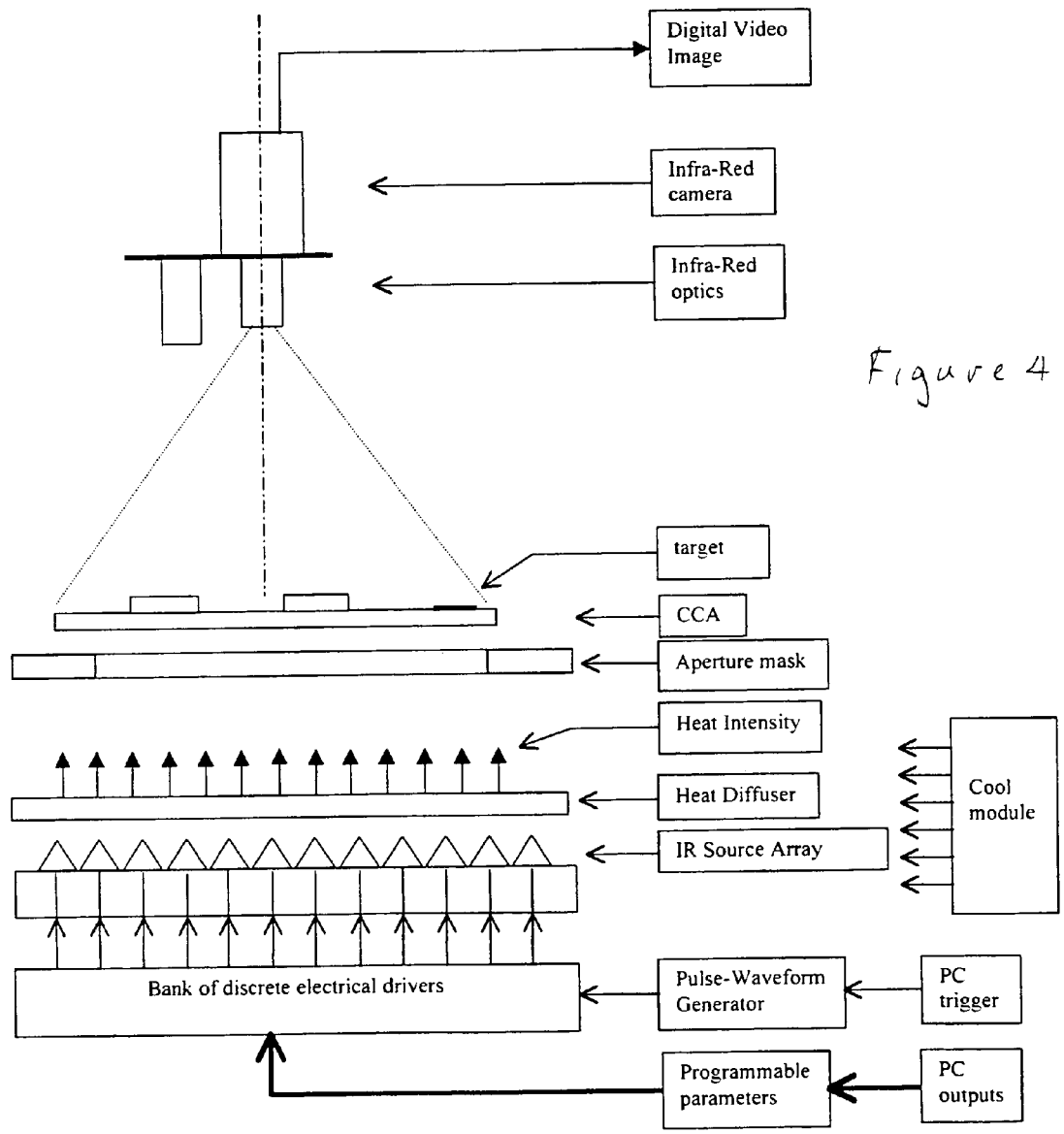
FIG. 4 illustrates in more detail in schematic block diagram fashion a system in accordance with the present invention.

FIG. 4 shows in a more detailed schematic block diagram form a system in accordance with the present invention. The system may be disposed in a housing and include means for supporting a sample in the housing during inspection.

As may be seen the infra-red optical component comprising an infra-red camera and associated infrared optics. The infrared optical system is disposed so as to monitor the heat profile of the one side of the sample to be tested.

The system also includes a thermal heat array which is disposed on the opposite side of the sample to be tested. The thermal heat array comprises a plurality of individually controllable heat source elements, i.e. the intensity of the energy being given off by each heat source element may be independently controlled or regulated.

A heat diffuser component is disposed between the sample to be tested and the thermal heat array. If desired or necessary this heat diffuser component may be omitted from the system; this may however require a more vigilante control by the computer system of the heater elements so as to obtain the desired thermal front wave.

As shown the example system may also include a mask element for masking or blocking heat energy from those parts of the sample which are not to be exposed to the energy being emitted from the thermal heat array. If desired or necessary this mask may be omitted from the system As mentioned above, the thermal heat array comprises a plurality of discrete thermal energy elements each of which may be independently regulated so as to emit energy of a desired intensity. Thus each element may, for example, be individually electrically controlled with respect to the amplitude, shape and duration of a heating duty cycle using a suitable or an appropriate electrical driver connected to computer. The parameters for each element are stored in the Computer (PC in FIG. 2). The thermal heat array may for example be built up using IR LED (Infra-Red Light Emitting Diodes) elements, Laser diode elements, miniature Quartz or incandescent filament lamp elements, etc. . . . ; in particular the thermal heating array may be composed of IR elements. Although the individual elements may each be separately controlled if desired the elements may be controlled in banks groups if so desired or necessary.

The thermal heater array may for example itself be composed of a plurality of juxtaposed basic array modules; for example each such basic array module of may be made up of an 8×8 array of elements, i.e. an array comprising eight columns and eight rows of heater elements, each column and row comprising eight heater elements (for a total of 64 elements).

Figure 5:
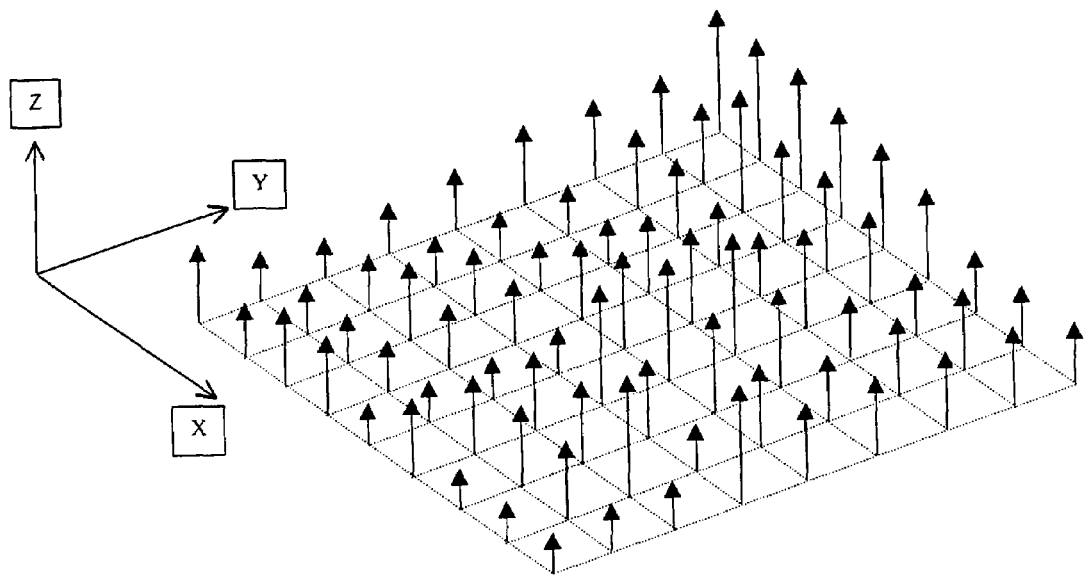
FIG. 5 illustrates un schematic fashion an array of discrete heat elements each element being shown in association with an intensity value.

FIG. 5 illustrates in schematic fashion the individual heat intensity developed by each individual heater element. For FIG. 2 the X and Y axis represent the plane of a thermal heater array, the intersection of a column and row representing a discrete heater (e.g. IR) element. The Z axis on the other hand represents the instantaneous heat intensity generated by each element; each arrow upstanding from an intersecting column and row being representative of a heat or energy intensity. Because each element is controlled independently by an electronic way, each element can generate a programmable intensity given by an analog signal through a driver amplifier. The duration of the pulse is also programmable.

The heat diffuser component is configured and disposed on the basis that it will permit or facilitate a more uniform, repeatable and plane (or contoured) heat wavefront than if such diffuser was not present. The heat diffuser component may for example take the form of a mesh or screen like element; it may for example be comprised of a certain number of layers of mesh screens (e.g. of silver, copper, stainless steel or any metal with low thermal conductivity coefficient); the mesh size may be of any suitable size keeping in mind the purpose is to obtain thermographic images.

A mask element for masking or blocking heat energy from those parts of the sample which are not to be exposed may if desired or required be exploited by the system. Such a masking component may be used to select an area where the heat has to pass through (aperture) and an area where the heat has to be blocked (mask). The mask element is to be of a thermally non-conductive material; it may for example be a non conductive thermal material such as of a Phenolic resin.

The thermal heater (e.g. IR) array module and the heat diffuser may as desired or required be subject to being cooled down to avoid any undesired increase in temperature outside the limits of the preheat process. This can be done by forced air with fans with/without TE cooler. The warm air will be evacuated outside the enclosure.

PASS/FAIL inspection for a Component at the micro inspection level (BGA for instance). To "see" the B GA balls (or any Flip-Chip pads), the spatial resolution has to be big enough to discriminate balls with defects (voids for instance) from standard "good!" balls. The optics should accommodate a board size of 1"×1".

The two optics can be mounted on a slide mechanism to be remotely selected.

The inspection process may for example proceed as follows:

First, it consists in a calibration process to determine the operational parameters of the unit. There are two calibration procedures:

3.2.1. First Calibration for the Bare (Blank) Board:

BB means a Blank (or Bare) Board with no Surface Mounted Components on either side.

A pre-selected area on this board is used as a temperature target to monitor the Bare Board temperature, 1. BB has to be between 20° C. and 25° C., before entering in the test enclosure.

2. BB on test enclosure fixture.

3. program all the heating elements at the same intensity level.

4. turn on all heating elements of the array.

5. monitor the IR radiation of the target (or temperature of the target) until it gets the Test Temperature (30° C. for instance).

6. when Test Temperature is reached, capture and record an image (average of 3 or more consecutive frames).

7. Compute all the IR radiations of the elements of the array and adjust their electrical driver to the lowest value. This will reduce all the other IR elements intensity. This will enable to get an uniform intensity wave passing through the board material and to compensate for the non uniformity of the IR array and the PCB material.

Second calibration for the populated board called CCA (Circuit Card Assembly); board with Surface Mounted Components on at least one (board) side thereof 1. Populated Board (CCA) has to be between 20° C. and 25° C., before entering in the test enclosure.
2. CCA on test enclosure fixture.
3. Program all the heating elements at the previously computed value, stored in the Computer.
4. Turn on all heating elements of the array.
5. Monitor the IR, radiation of the target (or temperature of the target) until it gets the Test Temperature (30° C. our example),
6. When Test Temperature is reached, capture and record the image (average of 3 or more consecutive frames),
7. Repeat all of the above process,
8. When sufficient number of CCA images have been captured (around 30 boards), the process will in the operational phase.

3.2.2. Operational Phase.

From the previous boards, the PC will compute the statistical or typical model to find the two limits for a pixel of the image. For process details please see U.S. Pat. Nos. 5,803,303 (Jerry Schlagheck) and 5,294,198 (Jerry Schlagheck), the entire contents of which are incorporate herein by reference. The building of the models and the Pass/Fail are explained in these patents.

4. Temperature Profile Over the Time.

Figure 6:
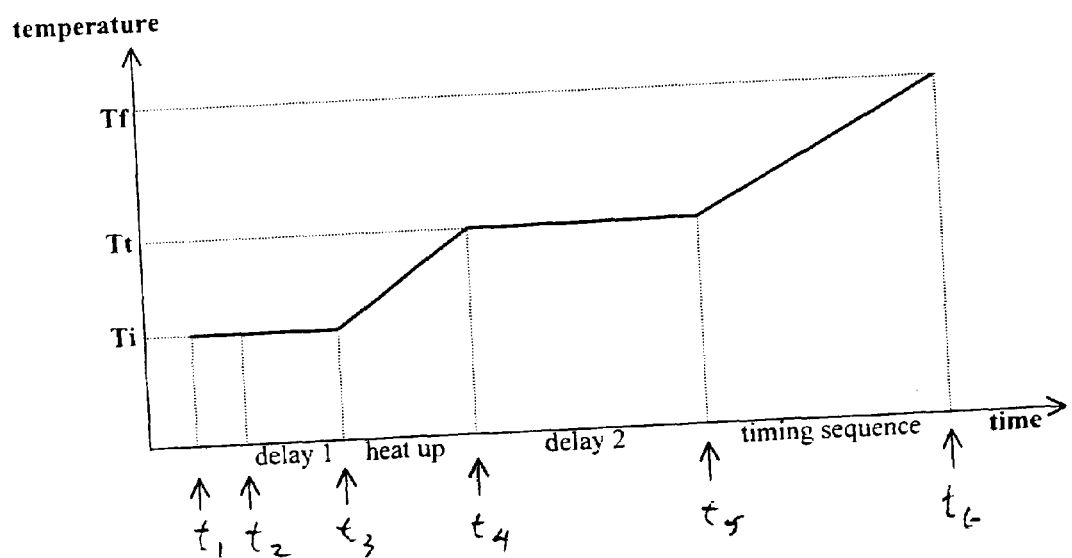
FIG. 6 is a graph showing a typical temperature evolution of a circuit board from the time the board is entering in a test enclosure. The board has to be at a temperature less than a testing enclosure in order to be heated by the heating elements.

This graph of FIG. 6 illustrates a typical temperature/time evolution of the board from the time the board is entering in a test enclosure, namely:

t1 is time install on inspection fixture;

t2 is time Start target monitoring;

t3 is time heat array placed ON; Continue target monitoring;

Tt is reached at Time t4; IR array is turned OFF; Capture Reference images;

t5 is time start Electrical Stimulation;

t6 is time Stop Electrical Stimulation; Capture Powered images;

For the graph in FIG. 6:

Ti: Initial Temperature of the board (between 20° C. and 25° C.)

Tt., Test Temperature at which the Reference image is captured (30° C. in our case)

TfFinal Temperature of the board after Electrical Stimulation.

delay 1: Time to initiate the process for heating the board- (around 20 msec)

heat up: Time the board will reach the Test temperature Tt (around 2 to 5 sec)

delay 2: Time to initiate the electrical stimulation signals sequence (around 20 msec).

Timing sequence, Time of the electrical stimulation sequence (between 5 and 20 sec)

2.6. Infra-Red Optics.

Depending of the device to be screened, the IR optics has to be changed to get the maximum resolution in the selected Field Of View.

PASS/FAIL inspection for a CCA (at the board level). To "see" the devices at the macro inspection level (CCA Infra-Red mode), the optics should accommodate a board size of 14"×14"

We claim:

1. A method for detecting a defect in a populated circuit board, said populated circuit board having a first side and an opposite second side, at least said first side being populated with one or more surface mounted components: said method comprising:
   1) directing a thermal wave at the second side of said populated circuit board
   2) recording a thermographic image of the first side of said populated circuit board once a surface thereof reaches a predetermined transit temperature or a predetermined transit time period has elapsed; and
   3) analyzing the obtained thermographic image by comparing the so obtained thermographic image with a standard thermographic image wherein
      a) the thermal wave is developed by a thermal heater array comprising a plurality of discrete individually controllable heat source elements, said elements each delivering a respective individual energy intensity reflecting the respective energy parameter information therefor comprised in a first block of energy parameter information;
      b) said first block of energy parameter information comprising, for each of said heat source elements, individual energy parameter information whereby the thermal heater-array may be induced to provide a thermal wave giving rise to a thermographic image indicative of uniform temperature of the surface of the first side of an predetermined unpopulated circuit board; and
      c) said standard thermographic image having been obtained by i) subjecting the second side of a predetermined populated circuit board to a thermal wave developed by said thermal heater array, said thermal field being applied until a surface of the first side of the predetermined populated circuit board reaches said predetermined transit temperature or said predetermined transit time period has elapsed, said elements of said thermal heater array each being set to deliver a respective individual energy intensity reflecting the energy parameter information of said first block of energy parameter information, and ii) taking said standard thermographic image from the first side of said predetermined populated circuit board once said predetermined transit temperature is reached or said predetermined transit time period has elapsed.

2. A method for detecting a defect in a populated circuit board, said populated circuit board having a first side and a second opposite side, at least said first side being populated with one or more surface mounted components, said method comprising:
   1) directing a thermal wave at the second side of the populated circuit board 2) recording a thermographic image of the first side of the populated circuit board once a predetermined transit temperature is reached on this side of the populated circuit board or a predetermined transit time period has elapsed; and
3) analyzing the obtained thermographic image by comparing the so obtained thermographic image with a standard thermographic image wherein the standard thermographic image has been obtained by
   a) monitoring the temperature of a surface of the first side of an predetermined unpopulated circuit board
   b) subjecting the second side of the unpopulated circuit board to a thermal wave developed by a thermal heater array comprising a plurality of discrete individually controllable heat source elements, said elements each being initially set to deliver an individual energy intensity such that the thermal array delivers a thermal wave of predetermined contour;
   c) adjusting the individual energy intensity of each of said elements until the thermal array delivers a thermal wave such that the surface being monitored provides a thermographic image thereof indicative of uniform temperature
   d) storing a first block of energy parameter information corresponding to the individual energy intensity of each of said heat source elements found to provide the recorded thermographic image indicative of uniform temperature
   e) monitoring the temperature of the first side of a predetermined populated circuit board
   f) subjecting the second side of the predetermined populated circuit board to a thermal wave developed by a thermal heater array comprising a plurality of discrete individually controllable heat source elements, said elements each being set to deliver a respective individual energy intensity reflecting the energy parameter information of said first block of energy parameter information, said thermal wave being applied until a surface site of the first side of the predetermined populated circuit board reaches said predetermined transit temperature or said predetermined transit time period has elapsed and taking a second thermographic image; and, if desired,
   g) storing a block of image information corresponding to the second thermographic image, said second thermographic image being Said standard thermographic image.

3. A method for detecting a defect in a populated sample having a thickness dimension substantially smaller than the length and width dimensions thereof, said populated sample having a first side and an opposite second side, at least said first side of said populated sample having one or more surface mounted components, said method comprising:
   1) directing a thermal wave at said second side of said populated sample
   2) recording a thermographic image of the first Side of said populated sample once a surface thereof reaches a predetermined transit temperature or a predetermined transit time period has elapsed; and
   3) analyzing the obtained thermographic image by comparing the so obtained thermographic image with a standard thermographic image wherein
      a) the thermal wave is developed by a thermal heater array comprising a plurality of discrete individually controllable heat source elements, said elements each delivering a respective individual energy intensity reflecting the respective energy parameter information therefor comprised in a first block of energy parameter information;
      b) said first block of energy parameter information comprising, for each of said heat source elements, individual energy parameter information whereby the thermal heater array may be induced to provide a thermal wave giving rise to a thermographic image indicative of uniform temperature of the surface of the first side of an unpopulated sample; and
      c) said standard thermographic image having been obtained by i) subjecting the second side of a predetermined populated sample to a thermal wave developed by said thermal heater array, said thermal field being applied until a surface of the first side of the predetermined populated sample reaches said predetermined transit temperature or said predetermined transit time period has elapsed, said elements of said thermal heater array each being set to deliver a respective individual energy intensity reflecting the energy parameter information of said first block of energy parameter information, and ii) taking said standard thermographic image from the 3 first side of the predetermined populated sample once said predetermined temperature is reached or said predetermined transit time has elapsed.

4. A method for detecting a defect in a populated sample having a thickness dimension substantially smaller than the length and width dimensions thereof, said sample having a first side and a second opposite side, at least said first side of said populated sample having one or more surface mounted components, said method comprising:
   1) directing a thermal wave at the second side of said populated sample
   2) recording a thermographic image of the first side of said populated sample once a predetermined transit temperature is reached on this side of the populated sample or a predetermined transit time period has elapsed; and
   3) analyzing the obtained thermographic image by comparing the so obtained thermographic image with a standard thermographic image, wherein the standard thermographic image has been obtained by
      a) monitoring the temperature of a surface of the first side of an predetermined unpopulated sample
      b) subjecting the second side of the unpopulated sample to a thermal wave developed by a thermal heater array comprising a plurality of discrete individually controllable heat source elements, said elements each being initially set to deliver an individual energy intensity such that the thermal array delivers a thermal wave of predetermined contour;
      c) adjusting the individual energy intensity of each of said elements until the thermal array delivers a thermal wave such that the surface being monitored provides a thermographic image thereof indicative of uniform temperature
      d) storing a first block of energy parameter information corresponding to the individual energy intensity of each of said heat source elements found to provide the recorded thermographic image indicative of uniform temperature
      e) monitoring the temperature of the first side of a predetermined populated sample
      f) subjecting the second side of the predetermined populated sample to a thermal wave developed by a thermal heater array comprising a plurality of discrete individually controllable heat source elements, said elements each being set to deliver a respective individual energy intensity reflecting the energy parameter information of said first block of energy parameter information, said thermal wave being applied until a surface site reaches a predetermined transit temperature or a predetermined transit time period has elapsed and taking a second thermographic image; and, if desired, g) storing a block of image information corresponding to the second thermographic image, said second thermographic image being said standard thermographic image.

5. A method for obtaining a standard thermographic image for use in detecting a defect in a populated circuit board, said populated circuit board having a first side and a second opposite side, at least said first side being populated with one or more surface mounted components, said method comprising:
   a) monitoring the temperature of a surface of the first side of an predetermined unpopulated circuit board
   b) subjecting the second side of the unpopulated circuit board to a thermal wave developed by a thermal heater array comprising a plurality of discrete individually controllable heat source elements, said elements each being initially set to deliver an individual energy intensity such that the thermal array delivers a thermal wave of predetermined contour,
   c) adjusting the individual energy intensity of each of said elements until the thermal array delivers a thermal wave such that the surface being monitored provides a thermographic image thereof indicative of uniform temperature
   d) storing a first block of energy parameter information corresponding to the individual energy intensity of each of said heat source elements found to provide the recorded thermographic image indicative of uniform temperature
   e) monitoring the temperature of the first side of a predetermined populated circuit board
   f) subjecting the second side of the predetermined populated circuit board to a thermal wave developed by a thermal heater array comprising a plurality of discrete individually controllable heat source elements, said elements each being set to deliver a respective individual energy intensity reflecting the energy parameter information of said first block of energy parameter information, said thermal wave being applied until a surface site of the first side of the predetermined populated circuit board reaches said predetermined transit temperature or said predetermined transit time period has elapsed and taking a second thermographic image; and, if desired,
   g) storing a block of image information corresponding to the second thermographic image, said second thermographic image being said standard thermographic image.

6. A method for obtaining a standard thermographic image for detecting a defect in a populated sample having a thickness dimension substantially smaller than the length and width dimensions thereof, said sample having a first side and a second opposite side, at least said first side of said populated sample having one or more surface mounted components, said method comprising
   a) monitoring the temperature of a surface of the first side of an predetermined unpopulated sample
   b) subjecting the second side of the unpopulated sample to a thermal wave developed by a thermal heater array comprising a plurality of discrete individually controllable heat source elements, said elements each being initially set to deliver an individual energy intensity such that the thermal array delivers a thermal wave of predetermined contour;
   c) adjusting the individual energy intensity of each of said elements until the thermal array delivers a thermal wave such that the surface being monitored provides a thermographic image thereof indicative of uniform temperature
   d) storing a first block of energy parameter information corresponding to the individual energy intensity of each of said heat source elements found to provide the recorded thermographic image indicative of uniform temperature
   e) monitoring the transit temperature of the first side of a predetermined populated sample
   f) subjecting the second side of the predetermined populated sample to a thermal wave developed by a thermal heater array comprising a plurality of discrete individually controllable heat source elements, said elements each being set to deliver a respective individual energy intensity reflecting the energy parameter information of said first block of energy parameter information, said thermal wave being applied until a surface site reaches a predetermined transit temperature or a predetermined transit time period has elapsed and taking a second thermographic image; and, if desired,
   g) storing a block of image information corresponding to the second thermographic image, said second thermographic image being said standard thermographic image.

\* \* \* \* \*